United States Patent [19]

Kedar et al.

[11] Patent Number: 5,722,470
[45] Date of Patent: Mar. 3, 1998

[54] BEAD DISPENSING DEVICE AND METHODS

[75] Inventors: Haim Kedar, Palo Alto; Robert M. Gavin, San José; Jeffrey H. Sugarman, Sunnyvale; Donald T. Roth, Mountain View, all of Calif.

[73] Assignee: Glaxo Group Limited, Greenford, United Kingdom

[21] Appl. No.: 555,799

[22] Filed: Nov. 9, 1995

[51] Int. Cl.⁶ .................................................. B65B 1/00
[52] U.S. Cl. ........................ 141/100; 141/9; 141/67; 141/130; 221/233; 221/236
[58] Field of Search ........................ 141/9, 67, 100, 141/105, 130; 221/233, 236

[56] References Cited

U.S. PATENT DOCUMENTS

| | | | |
|---|---|---|---|
| 2,540,059 | 1/1951 | Stim et al. | 222/345 |
| 2,755,008 | 7/1956 | Beltz et al. | 141/130 X |
| 3,874,431 | 4/1975 | Aronson | 141/129 |
| 4,244,863 | 1/1981 | Hemmerich et al. | 260/42.55 |
| 4,328,189 | 5/1982 | Haese et al. | 422/224 |
| 4,412,673 | 11/1983 | Ramsden et al. | 254/134.3 FT |
| 4,492,294 | 1/1985 | Ball | 141/96 X |
| 4,586,546 | 5/1986 | Mezei et al. | 141/67 X |
| 4,640,322 | 2/1987 | Ballester | 141/5 |
| 4,650,093 | 3/1987 | Meyer-Bosse | |
| 4,989,463 | 2/1991 | Cimaglia et al. | 141/97 X |
| 5,046,539 | 9/1991 | MacLeish et al. | 141/130 X |
| 5,366,122 | 11/1994 | Guentert et al. | 222/401 |
| 5,480,617 | 1/1996 | Uhlemann et al. | 422/140 |
| 5,488,567 | 1/1996 | Allen et al. | 364/497 |
| 5,500,348 | 3/1996 | Nishimura et al. | 435/7.24 |
| 5,503,805 | 4/1996 | Sugarman et al. | 422/131 |

FOREIGN PATENT DOCUMENTS

| | | |
|---|---|---|
| 949786 | 6/1974 | Canada. |
| 1 309 424 | 3/1973 | United Kingdom. |
| 1 420 364 | 1/1976 | United Kingdom. |

*Primary Examiner*—J. Casimer Jacyna
*Attorney, Agent, or Firm*—Darin J. Gibby; Lauren L. Stevens

[57] ABSTRACT

The invention provides methods and apparatus for transporting articles held within a liquid medium from one location to another. Apparatus according to the invention comprise a hopper having a top end, a bottom end, and at least one side wall extending therebetween. The bottom end includes an opening therein, and the hopper is adapted to receive the articles and the liquid medium. A means is provided for injecting an amount of the liquid medium into the hopper to fluidize the articles while held within the liquid medium. The apparatus further includes a container which may be aligned with the opening at the bottom end of the hopper. The container is sized to receive a known quantity of at least one of the articles.

36 Claims, 6 Drawing Sheets

BEAD DISPENSING DEVICE AND METHODS

BACKGROUND OF THE INVENTION

This invention relates generally to the field of transporting articles, and more particularly to transporting very small articles which are held within a liquid medium. In one particular aspect, the invention relates to transporting beads on which divers compounds have been synthesized.

Synthesizing processes where various compounds are placed on beads are described in, for example, U.S. patent application Ser. Nos. 08/149,675, filed Nov. 2, 1993 (Attorney Docket No. 16528J-004000) and 08/146,886, filed Nov. 2, 1993 (Attorney Docket No. 16528J-000730), the disclosures of which are herein incorporated by reference. After synthesis, it is often desirable to analyze the compounds synthesized on the beads. One such process is by placing the beads in an assay solution and observing whether a positive result occurs. For analysis, the beads often need to be transported from one location to another. For example, in one such process groups of beads are initially placed into a plurality of wells where a portion of the compound on the beads is photo released. Assays are then performed on each well. For wells producing a positive result, the groups of beads are then transferred into another well or are further divided and placed into a plurality of wells so that further testing can occur to identify the compound.

When handling such beads, the beads are usually held within a liquid medium, such as water, to help prevent (among other reasons) the beads from sticking together. Usually, such beads are very small, e.g. on the order of about 5 μm to 300 μm. Hence, transferring of such small beads from one location to another while held within a liquid medium is difficult and challenging. Transferring such small beads is especially challenging when a known quantity of beads, such as a single bead, must be individually transferred from a group of beads and placed in a test well.

It would therefore be desirable to provide methods and apparatus for transporting small articles from one location to another, particularly when the articles are held within a liquid medium.

SUMMARY OF THE INVENTION

The invention provides methods and apparatus for transporting articles from one location to another when the articles are held within a liquid medium. Apparatus according to the invention comprise a hopper having a top end, a bottom end having an opening therein, and at least one side wall extending between the top and bottom ends. The hopper is adapted to receive the articles and the liquid medium. A means is provided for injecting an amount of the liquid medium into the hopper to fluidize the articles while held within the liquid medium. The apparatus further includes a container which may be aligned with the opening at the bottom end of the hopper so that articles may exit the hopper from the opening and enter into the container. The container is sized to receive a known quantity of at least one of the articles. For example, the container may be sized and shaped to receive only a single article. Alternatively, the container may be sized and shaped to receive a specified range of articles at a time, such as, for example, 30 to 50 articles at a time.

In one preferable aspect, the hopper is tapered at the bottom end to assist in funneling the articles into the container. Preferably a vacuum source will be in communication with the container to assist in drawing the articles from the hopper and into the container. The apparatus preferably further includes a means for transferring the articles from the container. In one particular aspect, the container includes an open top and a bottom having at least one opening therein, and the container is formed within a rotatable member. With such a configuration, the means for transferring comprises a pressure source and a fluid line in communication with the bottom of the container. In this manner, the pressure source may be employed to force an amount of liquid through the fluid line and the container to expel the article out of the top of the container after the container has been rotated out of alignment with the opening at the bottom end of the hopper. In another aspect, a motor is preferably provided to rotate the rotatable member to move the container in and out of alignment with the hopper. In still a further aspect, the hopper is formed within a housing having an aperture therein, with the rotatable member being rotatably held within the aperture. With such a configuration, the means for injecting comprises the pressure source which forces liquid between the rotatable member and the housing and into the hopper while expelling the article from the container.

In an alternative embodiment, the container comprises a lumen or a tube, and the means for transferring comprises a pressure source which forces an amount of the liquid through the tube to expel the article from the tube. In another aspect, the hopper and the container are formed within a housing, and the means for injecting comprises the pressure source which forces an amount of the liquid medium into the hopper when forcing the liquid medium through the tube to expel the article. In one aspect, the tube may be sized and shaped to receive only a single article at a time. In a further aspect, a means is provided for viewing articles as they are expelled from the tube.

In a further alternative embodiment, the means for transferring comprises a threaded shaft having grooves therein so that rotation of the shaft will move the article within the grooves and along the shaft. In another aspect, the means for transferring further comprises a pressure source which forces an amount of the liquid medium past the article to expel the article. Preferably, the hopper is formed within a housing which includes an aperture for receiving the threaded shaft. The aperture includes an elongate slot along which the article is passed upon rotation of the threaded shaft. With such a configuration, the means for injecting preferably comprises the pressure source which forces an amount of the liquid medium through the elongate slot and into the hopper when expelling the article.

In a preferable aspect, the articles comprise beads. Usually, the beads are sized to be in the range from about 5 μm to 300 μm, more usually from about 10 μm to 200 μm. A plurality of test wells are preferably provided for receiving articles transported from the hopper. A translating mechanism may also be provided to translate the test wells so that a single well will receive the contents of the container each time the container is emptied. In a further aspect, a controller is provided for controlling pressure and vacuum provided by the pressure and vacuum sources. The controller is also in communication with the motor so that the controller may be employed to coordinate movement of the chamber with the pressure and vacuum. In still a further aspect, a hopper lid is provided for placement into the hopper. The hopper lid preferably includes at least one side wall which is sized and shaped to collect and trap bubbles existing on the hopper wall so that the bubbles will not attach to the articles and interfere with their dispersal from the hopper.

The invention provides an exemplary method for transporting articles held within a liquid medium. According to the method, the articles and the liquid medium are placed into a hopper having a bottom end having an opening therein. The articles are fluidized while within the hopper. A known quantity of at least one of the articles is funneled into a container positioned below and in alignment with the opening in the bottom end of the hopper. The article is then transferred from the container. In one aspect, the known quantity is a single article. Alternatively, the known quantity is a specified range of articles.

In one particularly preferable aspect, the container includes an open top and a bottom having at least one opening therein, and the transferring step comprises moving the container out of alignment with the opening in the bottom end of the hopper and forcing an amount of the liquid medium through the bottom of the container to expel the article. In another aspect, the chamber is formed within a rotatable member, and the rotatable member is rotated to move the chamber out of alignment with the opening in the bottom end of the hopper before the article is expelled.

In an alternative aspect, the container comprises a lumen or a tube, and the transferring step comprises forcing an amount of liquid through the tube to expel the article. Optionally, the article may be viewed as it is expelled from the tube. In still a further alternative aspect, the container comprises a groove in a threaded shaft, and the transferring step comprises rotating the shaft to move the at least one article along the shaft.

In one particular aspect, the fluidizing step comprises injecting an amount of the liquid medium into the hopper. Preferably, the liquid medium is injected through the bottom of the hopper. In yet another aspect, the hopper is tapered at the bottom end, and the funneling step comprises allowing the articles to settle within the hopper until the known quantity falls through the bottom of the hopper and into the container. Preferably, a vacuum will be created within the chamber to assist in drawing the known quantity from the hopper and into the container.

In still another aspect, the articles comprise beads having a size in the range from about 5 μm to 300 μm, more preferably from about 10 μm to 200 μm. Preferably, the liquid comprises water. In one particular aspect, the article is transferred to a test well. In still a further aspect, air bubbles which may exist on walls of the hopper are collected.

DETAILED DESCRIPTION OF THE SPECIFIC EMBODIMENTS

The invention provides methods and apparatus for transporting articles from one location to another while held within a liquid medium. Articles transported by the invention will be small, typically on the order of 5 μm to 300 μm, more usually from about 80 μm to 200 μm. The articles will usually comprise beads on which various compounds have been synthesized, such as by the processes described in U.S. patent application Ser. Nos. 08/149,675 and 08/146,886, previously incorporated by reference. The beads are usually constructed of a polymer such as polystyrene and polyethylene glycol. Such beads are commercially available from, for example, Nova Bio-chem.

Such beads will often be stored and transported while within a liquid medium, such as water, ethanol, methanol, buffer, DMSO, and the like. Such a liquid medium will preferably be less dense than the beads so that the beads will settle and sink within the medium. Among other reasons, the liquid medium helps prevent the beads from sticking or clumping together.

The methods and apparatus will be configured to transport a known quantity of articles. For instance, a single article may be removed from a larger group and individually transported to another location. Alternatively, a smaller group of a known quantity, e.g. about 30–50, may be removed from a larger group and transported to another location.

To transport the articles, the articles (while within the liquid medium) will preferably be placed into a hopper having an opening at a bottom end. Preferably, the hopper will be tapered at the bottom end so that the articles will tend to settle toward the opening. To assist in a uniform settlement of the articles within the hopper, the articles will preferably be fluidized. By fluidizing it is meant that the articles will be separated from each other while within the liquid medium so that as the articles settle within the hopper, they will tend to uniformly settle within the tapered end, without clumping together or forming a bridge across the bottom end to prevent any articles from exiting the bottom end. Usually, the articles will be fluidized by injecting an amount of the liquid medium into the hopper, preferably from the bottom end. Such a configuration is further advantageous in that it helps to insure that all articles will be dispensed from the hopper.

As the articles settle, they will fall from the hopper and into a container. Preferably, a vacuum will be provided to assist in drawing the articles out of the hopper. The container will preferably be sized to receive the known quantity of the articles. In this manner, the size of the container may be employed to assist in regulating the number of articles which are dispensed from the hopper at a time. After the container is filled with the known quantity, the container will be emptied and the remaining articles within the hopper will once again be fluidized so that the process may be repeated.

Figure 1:
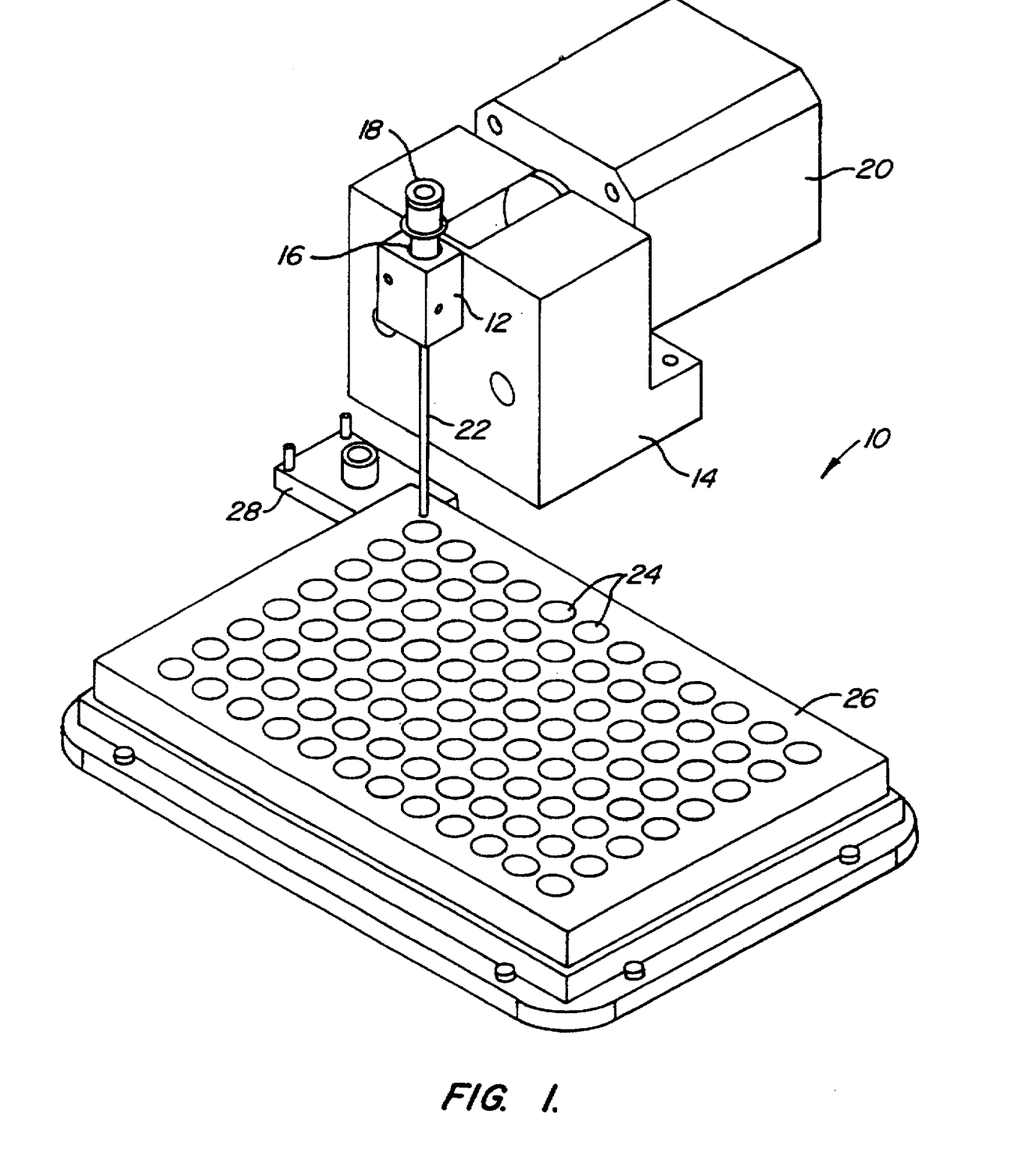
FIG. 1 is an isometric view of an exemplary apparatus for transporting articles held within a liquid medium according to the present invention.

Referring now to FIG. 1, an exemplary apparatus 10 for transporting beads held within a liquid medium will be described. The apparatus 10 includes a housing 12 that is removably attached to a frame 14. Formed within housing 12 is a hopper 16 into which beads and a liquid medium are initially placed. A lid 18 which may be placed over the top of the hopper is provided. A portion of the lid is slidable within the hopper 16. The apparatus 10 further includes a motor 20 which rotates a rotatable member shown in FIGS. 2 and 3 which in turn distributes the beads from the hopper 16 as described in greater detail hereinafter. Extending from housing 12 is a tube 22 through which dispensed beads are delivered to wells 24 of a multi-well plate 26. A translating mechanism 28 is provided which translates plate 26 so that each of the wells 24 may be separately aligned with tube 22 each time a known quantity of beads is distributed from the hopper 16.

Figure 2:
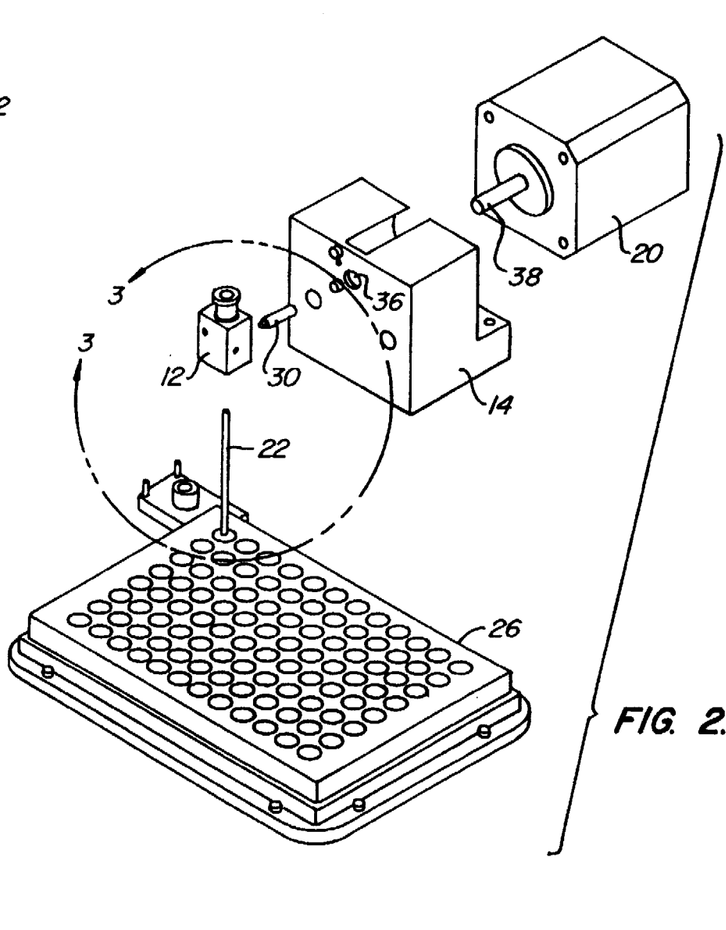
FIG. 2 is an exploded view of the apparatus of FIG. 1.
Figure 3:
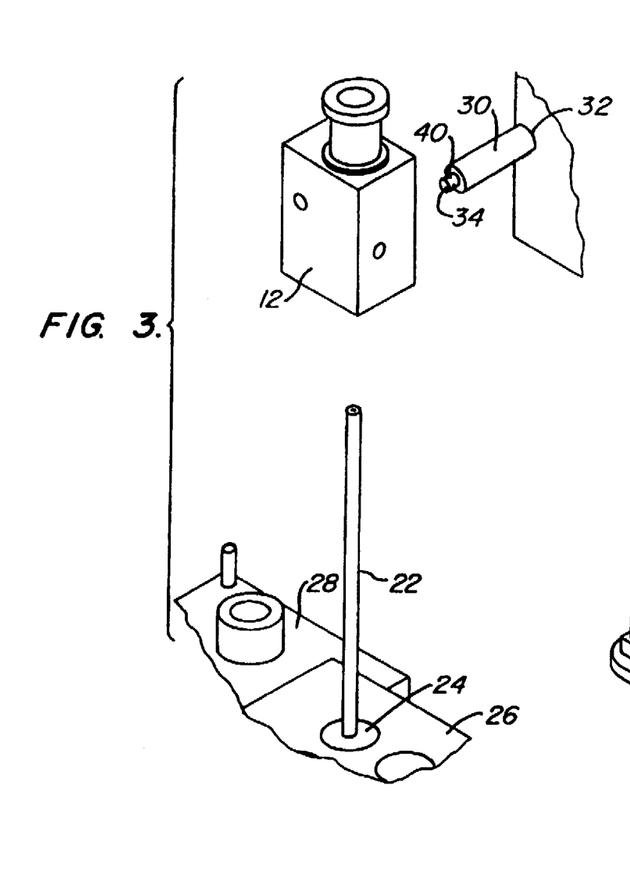
FIG. 3, is a more detailed view of the apparatus of FIG. 2 taken along lines 3—3.

Referring to FIGS. 2 and 3, construction of the apparatus 10 will be described in greater detail. Apparatus 10 further includes a rotatable member 30 having a proximal end 32 and distal end 34. Proximal end 32 extends through an aperture 36 in frame 14 where it is operably attached to a shaft 38 by a coupler (not shown) on motor 20. In this way, actuation of the motor 20 will cause rotatable member 30 to rotate.

Distal end 34 of rotatable member 30 is received within housing 12. Distal end 34 includes a container 40 which may be aligned with hopper 16 when rotatable member 30 is received within housing 12. Housing 12 and rotatable member 30 will preferably be constructed of a substantially transparent material, such as polycarbonate, so that the transfer of beads may be visualized. Visualization may be provided be employing a sensor, such as a laser sensor, or by image processing. In this manner, the transfer of beads from hopper 16 to container 40 may be confirmed. Alternatively, housing 12 and rotatable member 30 may be constructed of other, non-transparent materials.

Figure 4:
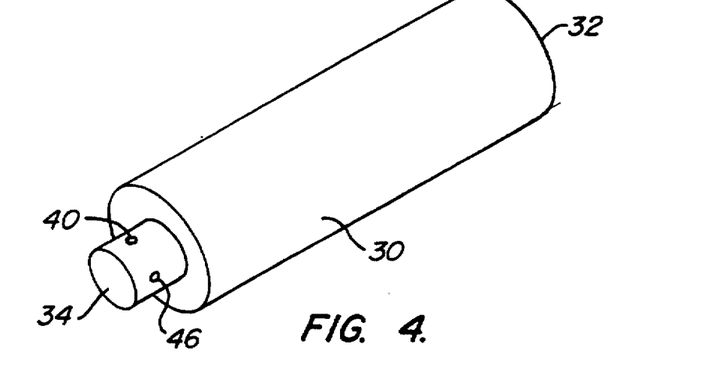
FIG. 4 is a perspective view of a rotatable member of the apparatus of FIG. 1.
Figure 5:
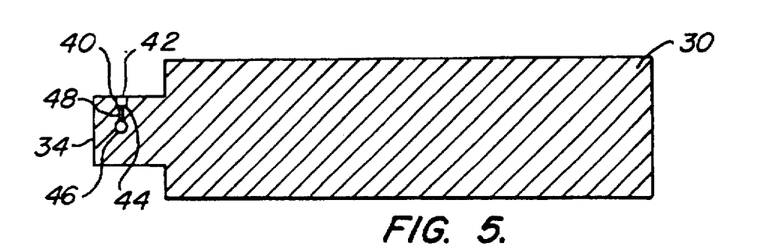
FIG. 5 is a cross sectional side view of the rotatable member of FIG. 4.

Referring to FIGS. 4 and 5, construction of rotatable member 30 will be described in greater detail. Container 40 is integrally formed within distal end 34 and is generally cylindrical in geometry (although other configurations are possible). Container 40 includes an open top end 42 and a bottom end 44 having an aperture therein. Ninety degrees from container 40 is a lumen 46 which is in communication with container 40 via a passage 48. As described in greater detail hereinafter, a vacuum or a pressure source may be placed in communication with lumen 46 to assist in drawing beads into container 40 or expelling them therefrom. Container 40 is preferably sized so that it will receive only a single bead at a time. In this manner, individual dispensing of beads from hopper 16 can be controlled by the size of container 40.

Figure 6:
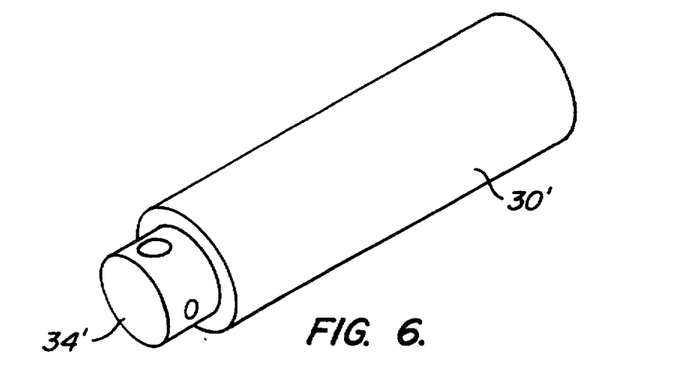
FIG. 6 is a perspective view of an alternative embodiment of a rotatable member.
Figure 7:
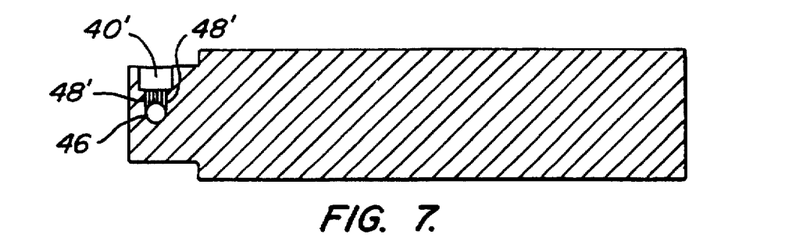
FIG. 7 is a cross sectional side view of the rotatable member of FIG. 6.

Shown in FIGS. 6 and 7 is an alternative embodiment of a rotatable member 30'. Rotatable member 30' is essentially identical to rotatable member 30 except for the configuration of distal end 34'. In rotatable member 30', container 40' is sized to receive a specific range of beads, e.g. 30 to 50 at a time. Since container 40' is larger than container 40, a plurality of passages 48' are provided to connect container 40' with lumen 46'. In this way, higher flow rate of fluid through container 40' is attained.

Figure 8:
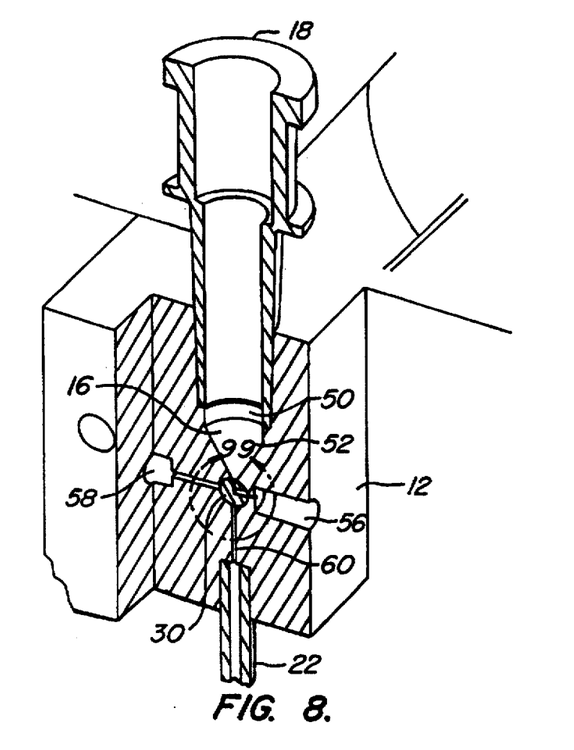
FIG. 8 is a cut-away perspective view of the apparatus of FIG. 1.
Figure 9:
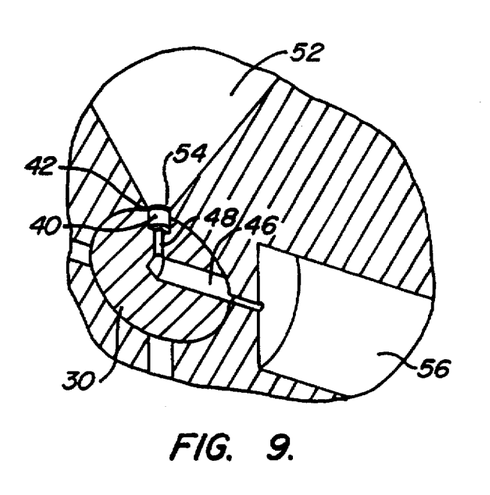
FIG. 9 is a more detailed view of the apparatus of FIG. 8 taken along lines 9—9.

Referring to FIG. 8, construction of housing 12 will be described in greater detail. Hopper 16 is integrally formed within housing 12 and has a generally cylindrical portion 50 and a generally cone-shaped bottom portion 52. As best shown in FIG. 9, bottom portion 52 includes an aperture 54 having a size which generally matches the size of open top 42 of container 40. The cone-shaped geometry of bottom portion 52 is advantageous in that it assists in funneling beads toward aperture 54 and into container 40.

Also formed within housing 12 is a vacuum port 56 and a pressure port 58. A vacuum source (not shown) will be connected to vacuum port 56 to assist in drawing beads from hopper 16 and into container 40. Pressure port 58 will be connected to a pressure source (not shown) which will serve to both fluidize the beads and within hopper 16 and to assist in expelling beads from container 40.

Figure 10:
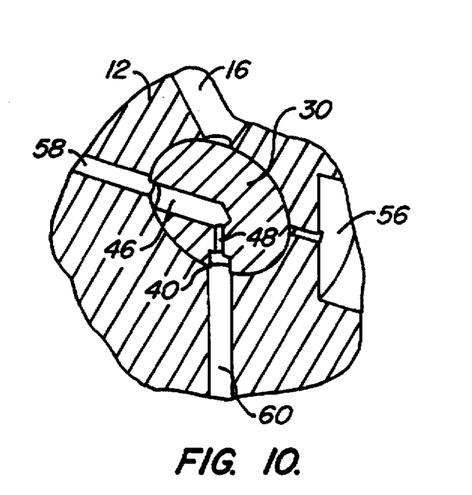
FIG. 10 illustrates the apparatus of FIG. 9, with the rotatable member being rotated 180 degrees, such as when expelling an article.

Referring to FIG. 9, operation of apparatus 10 to dispense a bead (or a known quantity of beads) from hopper 16 will be described. Initially, hopper 16 is filled with beads a liquid medium. Rotatable member 30 will be positioned to align container 40 with aperture 54. In this position, lumen 46 is aligned with vacuum port 56 as shown. A vacuum is then applied to vacuum port 56 to help draw one of the beads from hopper 16 into container 40. Passage 48 will be small enough so that a bead will be prevented from entering therein. After the bead is dispensed into container 40, rotatable member 30 is rotated 180° to the position shown in FIG. 10. In FIG. 10, container 40 is aligned with a lumen 60 which empties into tube 22 (see FIG. 8). In this position, lumen 46 of rotatable member 30 is aligned with pressure port 58. At this point, pressurized fluid is introduced through pressure port 58 to force fluid through lumen 46, passage 48, and container 40. The pressurized fluid expels the bead from container 40 and into lumen 60 where it passes into tube 22. From there, the dispensed bead will be placed into a well 24 of plate 26.

The tolerance between rotatable member 30 and housing 12 will be such that when pressurized fluid is forced through pressure port 58, some of the fluid will pass between housing 12 and rotatable member 30 and into hopper 16. In this manner, pressurized fluid will be forced upwardly through hopper 16 to fluidize the beads therein. Such fluidization prevents the beads in hopper 16 from clumping together or from forming bridges within bottom portion 15 which may prevent dispensing of beads through aperture 54. After fluidization, the beads settle uniformly within bottom portion 52 so that a single bead will be able to be dispensed through aperture 54. After the bead has been dispensed from container 40, rotatable member 30 is rotated 180° back to the position shown in FIG. 9 and the process is repeated. Preferably, a controller or microprocessor (not shown) will be provided to coordinate rotation of rotatable member 30 with the application of the vacuum and introduction of the pressurized fluid.

Referring back to FIG. 8, lid 18 will preferably be constructed such that a small tolerance will exist between lid 18 and hopper 16 when lid 18 is inserted therein. As lid 18 is pushed into hopper 16, air bubbles on the hopper walls will be trapped and collected by lid 18. In this way, undesirable attachment of the beads to the air bubbles will be prevented. Optionally, lid 18 may be constructed to be an extension of housing 12.

Figure 11:
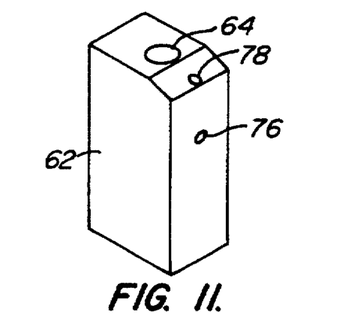
FIG. 11 is a perspective view of an alternative embodiment of an apparatus for transporting articles held within a liquid medium according to the present invention.
Figure 12:
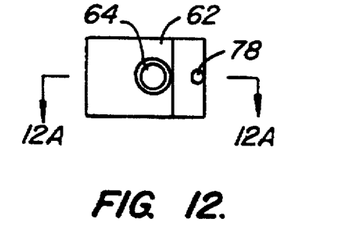
FIG. 12 is a top view of the apparatus of FIG. 11.
Figure 12A:
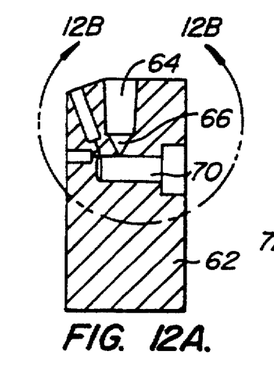
FIG. 12A is a cross-sectional view of the apparatus of FIG. 12 taken along lines A—A.
Figure 12B:
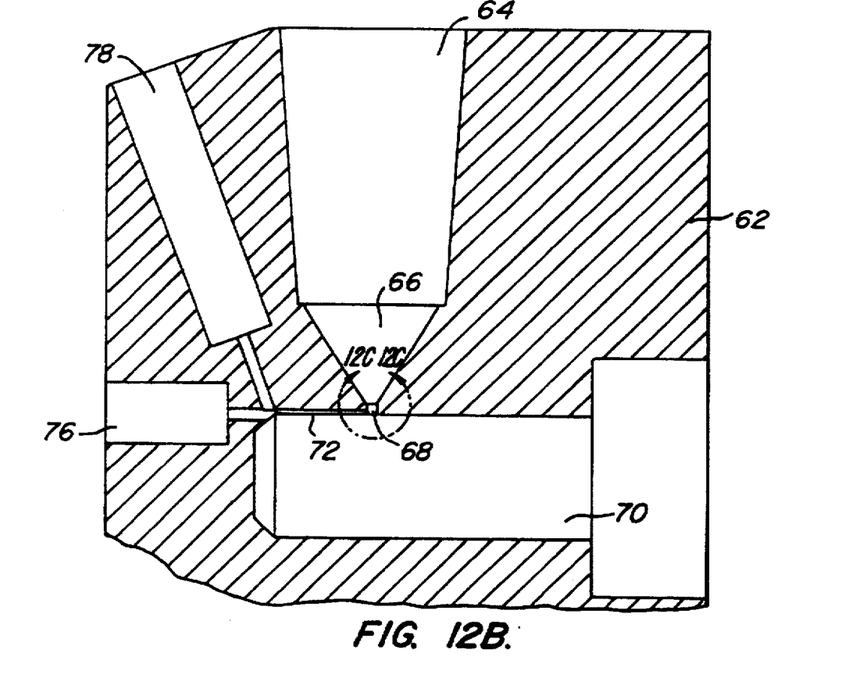
FIG. 12B is a more detailed view of the apparatus of FIG. 12A taken along lines B—B.
Figure 12C:
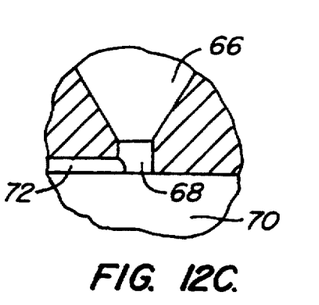
FIG. 12C is a more detailed view of the apparatus of FIG. 12B taken along lines C—C.
Figure 13:
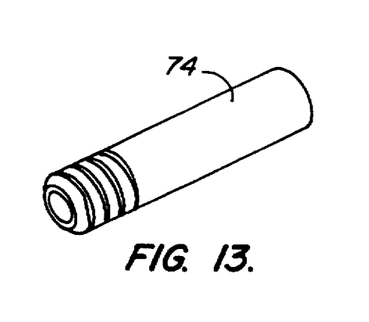
FIG. 13 is a perspective view of a threaded shaft for use the apparatus of FIG. 11 according to the present invention.
Figure 14:
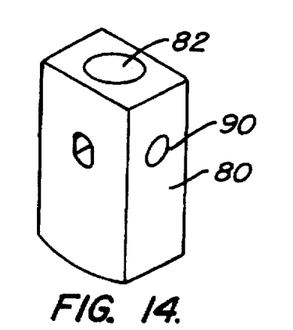
FIG. 14 is a perspective view of a further alternative embodiment of an apparatus for transporting articles held within a liquid medium according to the present invention.

Referring to FIGS. 11–13, an alternative embodiment of a housing 62 which may be used with apparatus 10 will be described. As best shown in FIG. 12B, housing 62 includes a hopper 64 having a cone-shaped bottom portion 66. As best shown in FIG. 12C, a container 68 is formed in housing 62 and is open to bottom portion 66. Container 68 is preferably sized to receive only a single bead at a time. Container 68 is also open to an elongate cylindrical opening 70 formed in housing 62. An elongate groove 72 is also formed in housing 62 and is open to both cylindrical opening 70 and container 68. Cylindrical opening 70 is sized and shaped to receive an elongate threaded shaft 74 as shown in FIG. 13.

With threaded shaft 74 in opening 70, a bead may be dispensed from hopper 64 as follows. Initially, a vacuum is applied from a vacuum port 76 in housing 62 which assists in drawing a bead from bottom portion 66 into container 68. As the bead settles into container 68, a portion of the bead sits within the threads of shaft 74. Shaft 74 is then rotated (such as by motor 20) to translate the bead along groove 72. When the bead reaches the end of groove 72, pressurized liquid is introduced through a pressure port 78 which moves the bead from housing 62 through vacuum port 76. From vacuum port 76, the bead may be delivered to a test well. Introduction of pressurized liquid through port 78 also serves to fluidize beads within hopper 64. Specifically, some of the liquid passes through groove 72, into container 68, and upward into bottom portion 66. After fluidization, container 68 may be refilled with another bead and the process repeated.

Figure 15:
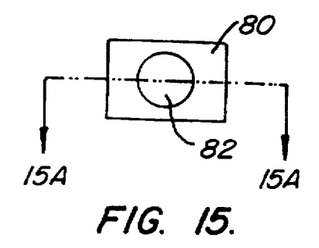
FIG. 15 is a top view of the apparatus of FIG. 14.
Figure 15A:
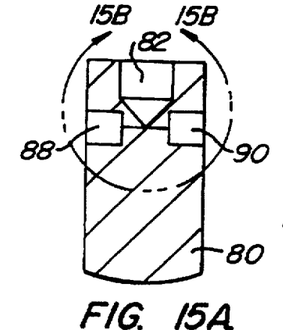
FIG. 15A is a cross-sectional view of the apparatus of FIG. 14 taken along lines A—A.
Figure 15B:
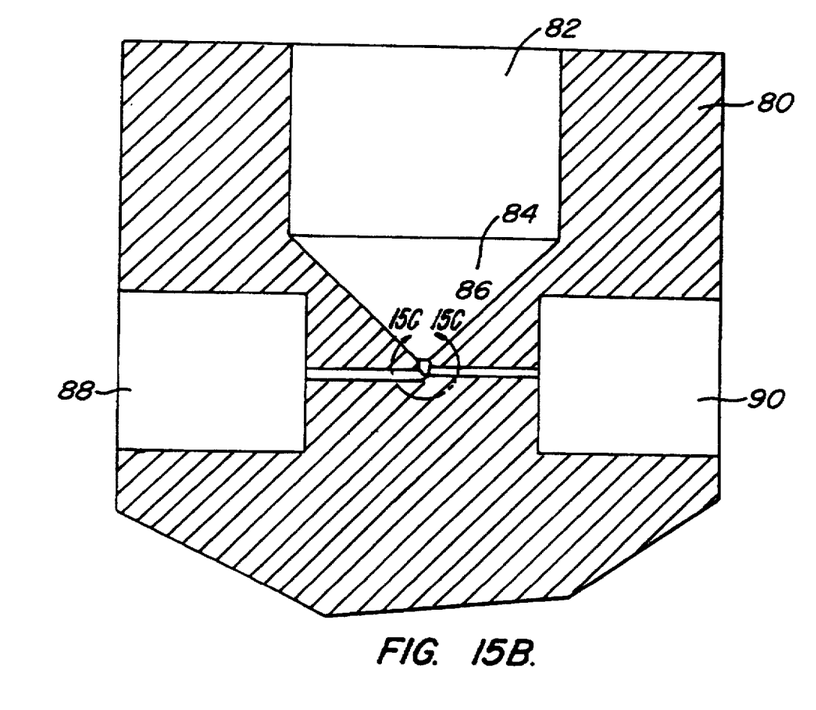
FIG. 15B is a more detailed view of the apparatus of FIG. 15A taken along lines B—B.
Figure 15C:
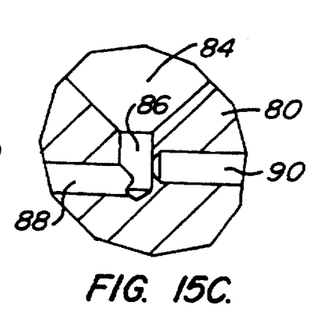
FIG. 15C is a more detailed view of the apparatus of FIG. 15B taken along lines C—C.

Referring to FIGS. 14, 15, and 15A–15C, another alternative embodiment of a housing 80 that may be used with apparatus 10 will be described. As best shown in FIG. 15B, housing 80 includes a hopper 82 having a generally cone-shaped bottom portion 84. Bottom portion 84 empties into a container 86. Container 86 is preferably cylindrical in geometry and has a diameter sized such that only a single bead can enter therein at a time. Housing 80 includes an exit port 88 and a pressure port 90. Ports 88 and 90 are in communication with the container 86 and assist in dispensing beads from hopper 82 as follows. Initially, with the assistance of gravity, a bead is drawn from bottom portion 84 into container 86. As a bead enters container 86, pressurized fluid is introduced through port 90 to force the bead from container 86 and into exit port 88 where it may be dispensed into a test well. As best shown in FIG. 15C, exit port 88 is at atmospheric pressure so that pressurized fluid from port 90 will force the bead into port 88. At the same time, some of the pressurized fluid will be forced into bottom portion 84 to fluidize the articles held therein. After fluidization, the beads are allowed to settle and one will drop into container 86 and out through exit port 88. A sensor, such as a laser sensor, may be employed to confirm placement of a bead into the container 86.

The invention has now been described in considerable detail for purposes of understanding. However, alternative uses for the invention will occur to those of skill in the art. Therefore, the above description should not be taken as limiting the scope of the invention. Instead, the scope of the invention should be determined chiefly with reference to the appended claims, along with a full scope of equivalents to which those claims are entitled.

What is claimed is:

1. A method for transporting article held within a liquid medium, the method comprising:
   placing the articles and the liquid medium into a hopper having a bottom end with an opening therein;
   fluidizing the articles while within the hopper such that the articles are uniformly distributed within the hopper;
   funneling a single article into a container positioned below and in alignment with the opening in the bottom end of the hopper; and
   transferring the article from the container.

2. A method as in claim 1, wherein the container includes an open top and a bottom having at least one opening therein, and wherein the transferring step comprises moving the container out of alignment with the opening in the bottom end of the hopper and forcing an amount of the liquid medium through the bottom of the container to expel the article.

3. A method as in claim 2, wherein the chamber is formed within a rotatable member, and wherein the rotatable member is rotated to move the chamber out of alignment with the opening in the bottom end of the hopper before the article is expelled.

4. A method as in claim 1, wherein the container comprises a tube, and wherein the transferring step comprises forcing an amount of liquid through the tube to expel the article.

5. A method as in claim 4, further comprising viewing the article as it is expelled from the tube.

6. A method as in claim 1, wherein the container comprises a groove in a threaded shaft, and wherein the transferring step comprises rotating the shaft to move the article along the shaft.

7. A method as in claim 1, wherein the fluidizing step comprises injecting an amount of the liquid medium into the hopper.

8. A method as in claim 7, wherein the liquid medium is injected through the bottom of the hopper.

9. A method as in claim 1, wherein the hopper is tapered at the bottom end, and wherein the funneling step comprises allowing the article to settle within the hopper until the article falls through the bottom the hopper and into the container.

10. A method as in claim 9, wherein the funneling step further comprises creating a vacuum within the container to assist in drawing the article into the container.

11. A method as in claim 1, wherein the article comprises a bead having a size in the range from about 5 µm to 300 µm.

12. A method as in claim 11, wherein the liquid comprises water.

13. A method as in claim 1, wherein the article is transferred to a test well.

14. A method as in claim 1, further comprising collecting air bubbles which may exist on walls of the hopper.

15. An apparatus for transporting an article held within a liquid medium, the apparatus comprising:
   a hopper having a top end, a bottom end, and at least one side wall extending there between, the bottom end having an opening therein, wherein the hopper is adapted to receive articles and the liquid medium;
   means for injecting an amount of the liquid medium into the hopper to fluidize the articles while held within the liquid medium and to uniformly distribute the articles within the hopper; and
   a container which may be aligned with the opening at the bottom end of the hopper, wherein the container is sized to receive a single article.

16. An apparatus as in claim 15, wherein the hopper is tapered at the bottom end.

17. An apparatus as in claim 15, further comprising means for transferring the articles from the container.

18. An apparatus as in claim 17, wherein the container includes an open top and a bottom having at least one opening therein, wherein the container is formed within a rotatable member, and wherein the means for transferring comprises a pressure source and a fluid line in communication with the bottom of the container, wherein the pressure source forces an amount of the liquid through fluid line and the container to expel the at least one article out of the top of the container after the container is rotated out of alignment with the opening at the bottom end of the hopper.

19. An apparatus as in claim 18, further comprising a motor which rotates the rotatable member.

20. An apparatus as in claim 18, wherein the hopper is formed within a housing, and wherein the housing includes an aperture having the rotatable member rotatably held therein, and wherein the means for injecting comprises the pressure source which forces liquid between the rotatable member and the housing and into the hopper while expelling the article from the container.

21. An apparatus as in claim 17, wherein the container comprises a tube, and wherein the means for transferring comprises a pressure source which forces an amount of liquid through the tube to expel the article from the tube.

22. An apparatus as in claim 21, wherein the hopper and the container are formed within a housing, and wherein the means for injecting comprises the pressure source which forces an amount of the liquid medium into the hopper when forcing the liquid medium through the tube to expel the article.

23. An apparatus as in claim 21, further comprising means for viewing the article as it is expelled from the tube.

24. An apparatus as in claim 17, wherein the means for transferring comprises a threaded shaft having grooves therein so that rotation of the shaft will move the article within the grooves and along the shaft.

25. An apparatus as in claim 24, wherein the means for transferring further comprises a pressure source which forces an amount of the liquid medium past the article to expel the article.

26. An apparatus as in claim 25, wherein the hopper is formed within a housing, wherein the housing includes an aperture for receiving the threaded shaft, wherein the aperture includes an elongate slot along which the article is passed upon rotation of the threaded shaft, and wherein the means for injecting comprises the pressure source which forces an amount of the liquid medium through the elongate slot and into the hopper when expelling the article.

27. An apparatus as in claim 24, wherein the means for transferring further comprises a vacuum source which draws an amount of the liquid medium past the article to expel the article.

28. An apparatus as in claim 15, wherein the article is a bead.

29. An apparatus as in claim 28, wherein the bead is sized in the range from 5 µm to 300 µm.

30. An apparatus as in claim 15, further comprising a plurality of test wells for receiving article transported from the hopper.

31. An apparatus as in claim 30, further comprising a translating mechanism which translates the test wells so that a single well will receive the contents of the container each time the container is emptied.

32. An apparatus as in claim 15, further comprising a vacuum source in communication with the container which assists in drawing the article into the container.

33. An apparatus as in claim 32, wherein the means for injecting comprises a pressure source, and further comprising a controller which controls pressure or vacuum delivery.

34. An apparatus as in claim 33, wherein the controller coordinates movement of the container with pressure or vacuum delivery.

35. An apparatus as in claim 15, further comprising a hopper lid which may be placed over the top of the hopper and wherein a portion of the lid is slidable within the hopper.

36. An apparatus as in claim 35, wherein the hopper lid includes at least one side wall which is sized and shaped to collect and trap bubbles existing on the hopper wall.

* * * * *